(12) United States Patent
Willuweit et al.

(10) Patent No.: US 8,582,103 B2
(45) Date of Patent: Nov. 12, 2013

(54) BULBLESS SPECTROMETER (75) Inventors: Thomas Willuweit, Hof (DE); Achim Sack, Erlangen (DE); Ralf Griesbach, Hof (DE)

(73) Assignee: IFE Innovative Forschungs- und Etwicklungs GmbH & Co. KG, Harrislee (DE)

( * ) Notice: Subject to any disclaimer, the term of this patent is extended or adjusted under 35 U.S.C. 154(b) by 0 days.

(21) Appl. No.: 13/375,396

(22) PCT Filed: Jun. 17, 2010

(86) PCT No.: PCT/EP2010/058533
§ 371 (c)(1),
(2), (4) Date: Feb. 9, 2012

(87) PCT Pub. No.: WO2010/146110
PCT Pub. Date: Dec. 23, 2010

(65) Prior Publication Data
US 2012/0140227 A1 Jun. 7, 2012

(30) Foreign Application Priority Data

Jun. 17, 2009 (DE) .......................... 10 2009 025 261

(51) Int. Cl.
*G01N 21/25* (2006.01)
*G01N 21/00* (2006.01)
(52) U.S. Cl.
USPC ............ 356/413; 356/432; 356/433; 356/434
(58) Field of Classification Search
USPC .......................... 356/432–343, 326, 436–442
See application file for complete search history.

(56) References Cited

U.S. PATENT DOCUMENTS

| | | | |
|---|---|---|---|
| 5,754,294 A * | 5/1998 | Jones et al. .................... | 356/503 |
| 6,044,329 A * | 3/2000 | Kidd ............................... | 702/28 |
| 6,526,298 B1 * | 2/2003 | Khalil et al. ................... | 600/310 |
| 7,358,476 B2 * | 4/2008 | Kiesel et al. ................ | 250/208.2 |
| 7,369,239 B2 | 5/2008 | Nagashima et al. | |

(Continued)

FOREIGN PATENT DOCUMENTS

| | | |
|---|---|---|
| DE | 28 38 498 C2 | 9/1982 |
| DE | 84 07 054 U1 | 6/1984 |

(Continued)

OTHER PUBLICATIONS

"Probenehmer 14 Stationaere und Portable Probenemer," Internet Citation, <http://www.hach-lange.de/common/documents/1005/1009/10544_Ebook_D_HL_Katalog_Tell4.pdf>pp. 108-109 (Jan. 1, 2004).

(Continued)

*Primary Examiner* — Tarifur Chowdhury
*Assistant Examiner* — Sunghee Y Gray
(74) *Attorney, Agent, or Firm* — Jenkins, Wilson, Taylor & Hunt, P.A.

(57) ABSTRACT

The present invention creates a spectrometer (1; 1') for measuring the concentration of at least one analyte in a fluid sample (2; 2'), with a light source (3; 3') to generate a light beam (4; 4'), with a photosensor (5; 5') to receive the light beam (4; 4'), and with a measurement length (6; 6'), in which the fluid sample (2; 2') can be placed, in the beam path of the light beam (4; 4'), the measurement length (6; 6') being provided in changeable form.

17 Claims, 4 Drawing Sheets

(56) References Cited

U.S. PATENT DOCUMENTS

| | | | |
|---|---|---|---|
| 7,940,388 B2* | 5/2011 | Bungo | 356/319 |
| 2005/0254053 A1 | 11/2005 | Wright | |
| 2005/0254054 A1 | 11/2005 | Janni | |
| 2008/0067328 A1 | 3/2008 | Fujita | |
| 2010/0208256 A1* | 8/2010 | Tang et al. | 356/326 |

FOREIGN PATENT DOCUMENTS

| | | | |
|---|---|---|---|
| DE | 93 19 749 U1 | | 2/1994 |
| DE | 10 2006 004 916 | | 6/2007 |
| EP | 1 489 403 | | 12/2004 |
| EP | 1 792 653 | | 6/2013 |
| WO | WO02/060320 | | 8/2002 |
| WO | WO 2007/088047 | * | 8/2007 |
| WO | WO 2008/124542 | | 10/2008 |
| WO | WO2010/146110 | | 12/2010 |

OTHER PUBLICATIONS

International Search Report corresponding to International Patent Application No. PCT/EP2010/058533 dated Oct. 12, 2010.

Notification Concerning Transmittal of International Preliminary Report on Patentability (Chapter I of the Patent Cooperation Treaty) corresponding to International Patent Application No. PCT/EP2010/058533 dated Jan. 5, 2012.

Written Opinion corresponding to International Patent Application No. PCT/EP2010/058533 dated Dec. 17, 2011.

Notification of Acceptance of South Africa Patent Application No. 2011/09044 dated Jun. 8, 2012.

Official Action corresponding to New Zealand Patent Application No. 596659 dated Oct. 25, 2012.

Official Action corresponding to Chinese Patent Application No. 201080027051.3 dated Feb. 18, 2013.

Abstract of Chilean Patent Application No. 1790-1996.

Certificate of Grant corresponding to South African Patent Application No. 2011/09044 dated Aug. 29, 2012.

Examination Report corresponding to Chilean Patent Application No. 3153-2011 dated Apr. 13, 2013.

Decision to Grant corresponding to Mexican Patent Application No. MX/2013/038492 dated Jun. 5, 2013.

Official Action corresponding to Colombian Patent Application No. 11-171561-4 dated May 9, 2013.

* cited by examiner

BULBLESS SPECTROMETER

Application Ser. No. 13/375,396 is a national stage entry of PCT/EP2010/058533 filed Jun. 17, 2010. Applicants claim, under 35 U.S.C. §119, the benefit of priority of the filing date of Jun. 17, 2009 of a German patent application, copy attached, Serial Number 10 2009 025 261.4, filed on the aforementioned date, the entire contents of which is incorporated herein by reference.

The present invention concerns a bulbless spectrometer.

Spectrometers for measuring the concentration of at least one analyte in a fluid sample are generally known. The measurement method on which spectrometers are based depends on the known physical phenomenon that a light beam is weakened (extinguished) when it penetrates a fluid. The weakening is proportional to the concentration of the analyte and to the measurement length, in the fluid, which the light beam must penetrate. This physical relationship is described by the Lambert-Beer extinction law.

Known spectrometers such as are described in published specification DE 28 38 498 C2 involve devices which are of comparatively large dimensions and are operated in a stationary position in the laboratory. In order to measure the concentration of an analyte in a fluid sample using known spectrometers, the fluid sample must first be put into a bulb, which is then arranged in the corresponding spectrometer.

With the approach described above, it has been shown to be disadvantageous that commercially available bulbs define a fixed measurement length, which is determined by the plane-parallel lateral faces of a bulb. However, if a greater measurement length is required, e.g. in the case of very low concentrations of the analyte in the fluid sample, a correspondingly differently dimensioned bulb must be used. This is relatively laborious. Additionally, bulbs easily become dirty by being touched by fingers, or are easily dropped accidentally and smashed.

The object of the present invention is therefore to provide an improved spectrometer which, in particular, avoids the described laborious handling of the bulbs.

This object is achieved by a bulbless spectrometer according to Claim 1.

Accordingly, a bulbless spectrometer for measuring the concentration of at least one analyte in a fluid sample is provided, and has the following: a light source to generate a light beam, a photosensor to receive the light beam, and a measurement length, in which the fluid sample can be placed, in the beam path of the light beam, the measurement length being provided in changeable form.

The idea on which the present invention is based is to do completely without using bulbs, and at the same time to provide a changeable measurement length.

The laborious handling of the bulbs is thus omitted, and at the same time it is made possible to measure very high and very low concentrations of an analyte in a fluid sample.

The subclaims give advantageous versions and further developments of the present invention.

A "fluid" here should be understood as a liquid, a gas or a mixture of them. Preferably, a fluid can also have a solid part.

Preferably, "light" here does not only mean visible light, but also, for example, infrared, UV or X-ray radiation.

According to a preferred further development of the spectrometer according to the invention, the light source and the photodetector are provided so that they can move relative to each other in order to change the measurement length. In this way, the measurement length can easily be changed.

According to another preferred further development of the spectrometer according to the invention, the measurement length between the light source or the photosensor and an optical waveguide arranged in the beam path is defined, the light source and the optical waveguide and/or the photosensor and the optical waveguide being provided so that they can move relative to each other in order to change the measurement length. In this way too, the measurement length can easily be changed.

According to another preferred further development of the spectrometer according to the invention, the optical waveguide extends into a sleeve, the measurement length being formed between one face of the optical waveguide and an end piece of the sleeve, and being changeable by moving the sleeve and the optical waveguide relative to each other. Thus the measurement length can be changed either by pushing the optical waveguide further into the sleeve, which remains stationary relative to a spectrometer handling part, which will be described in more detail below, or by the sleeve being pushed further onto the optical waveguide, which is provided so that it is stationary relative to the above-mentioned handling part. "Face" means the end of the optical waveguide, where the light beam enters or emerges.

According to another preferred further development of the spectrometer according to the invention, the sleeve has at least one opening, which makes it possible to place the fluid sample in the measurement length. In this way, the fluid sample can easily be placed in the measurement length. This also makes it easily possible to provide the spectrometer as an immersion spectrometer. "Immersion spectrometer" means that to take a fluid sample from a fluid, a section of the spectrometer is immersed in the fluid, and the fluid sample is taken from the fluid in this way.

According to another preferred further development of the spectrometer according to the invention, along the beam path two of the openings are provided in the sleeve at a distance from each other. In this way, in the case that a large measurement length is provided, the correspondingly large fluid sample can be placed in the measurement length relatively quickly.

According to another preferred further development of the spectrometer according to the invention, the optical waveguide is attached permanently to a handling part of the spectrometer, and/or the sleeve extends in sections in a receiving region in the handling part, and is provided so that it can move within the receiving region. In this way, the spectrometer can easily be held by one hand on its handling part, an operator being able to move the sleeve relative to the optical waveguide with the other hand, and thus change the measurement length. It should be pointed out that this moving of the sleeve relative to the optical waveguide, and the ability to move the light source and the photodetector relative to each other, can be provided in stages, e.g. by means of appropriate catches, or in continuously adjustable form.

According to another preferred further development of the spectrometer according to the invention, the and piece of the sleeve has a lens and/or the photosensor. Preferably, the lens delimits the measurement length, opposite the face of the optical waveguide. Also preferably, the lens receives the light from the face of the optical waveguide and focuses it on the photosensor. This means that from the point of view of the optical waveguide, the photosensor is arranged behind the lens. The photosensor is preferably in the form of a photodiode. Photodiodes convert light into electric current, exploiting the photoelectric effect.

According to another preferred further development of the spectrometer according to the invention, the light source couples in the light beam on the other face of the optical waveguide. Accordingly, the light source is preferably arranged in the handling part.

According to another preferred further development of the spectrometer according to the invention, the optical waveguide is in the form of an acrylic bar, MacroIon bar, glass bar or glass fibre cable. Such glass fibre cables are easily obtained, and also stand out in that, for example, within the handling part they can be guided to the light source on a path which is not straight.

According to another preferred further development of the spectrometer according to the invention, a first and a second light source are provided, so that the light beam can be generated with a first or a second wavelength/wavelength range according to choice. The first and second wavelengths are different from each other. The same applies to the wavelength ranges. However, the wavelength ranges can overlap. Depending on the fluid sample or analyte of which the concentration is to be measured, it can be a requirement that different wavelengths or different wavelength ranges are required for carrying out an appropriate measurement. Whether it is the first or the second light source that generates the light beam can be set manually by a user, for example. Alternatively, the setting can be automated by means of a controller of the spectrometer. In particular, the choice between the first or second light source can be made depending on a selected analysis mode, which is explained in more detail below. Of course, more than two light sources can also be provided. Preferably, the one or more light sources emit almost monochromatic light, with a wavelength range of 250-5000 nm.

According to another preferred further development of the spectrometer according to the invention, the one or more light sources are in the form of LEDs, in particular laser diodes. A laser diode is a LED which generates laser radiation.

According to another preferred further development of the spectrometer according to the invention, a controller is provided. In a first step, it controls the one or more light sources and the photosensor so as to determine a characteristic of the fluid sample, in a second step it selects one of multiple analysis modes, which are stored in a memory of the spectrometer, depending on the characteristic, and in a third step it controls the one or more light sources and the photosensor depending on the selected analysis mode. An analysis mode here contains one or more instructions for determining the concentration of an analyte in the fluid sample in a recognised, repeatable and comparable manner. For example, these instructions can define the calibration or the wavelength of the light beam to be used. The "characteristic" means, in particular, a characteristic absorption spectrum of the fluid or of the analyte in the fluid; this is also called the "spectral fingerprint".

According to another preferred further development of the spectrometer according to the invention, it is in portable form. This means that the dimensions of the spectrometer are such that they make carrying and handling the spectrometer manually possible, and that the spectrometer does not have to be connected to a table, e.g. a laboratory bench, or another support.

According to another preferred further development of the spectrometer according to the invention, it is in mains-independent form. This means that the spectrometer does not have to be connected to a mains power supply, but has an energy source which is integrated in the spectrometer. The energy source which is integrated in the spectrometer can be a non-rechargeable or rechargeable battery.

Additionally, a use of the spectrometer according to the invention for determining a volume of a fluid (called the first fluid below) in a vessel is provided.

A "vessel" should be understood here as any kind of receptacle for receiving a fluid of defined volume. Accordingly, the term "vessel" here includes any kind of container, pond boundary, etc.

For this purpose, first a second fluid with a known volume and a known concentration of an analyte is put into the vessel, and then mixes with the first fluid.

The concentration of the analyte in the mixture of the first and second fluids is then measured using the spectrometer.

The spectrometer then determines, on the basis of the concentration of the analyte in the mixture, the volume of the first fluid. For this purpose, previously the known volume of the second fluid and the known concentration of the analyte in the second fluid are provided to the spectrometer. The concentration of the analyte in the second fluid can also be determined using the spectrometer.

Furthermore, a portable bulbless immersion spectrophotometer for determining analyte concentrations in fluid samples is provided, with
a) a light source and a photodetector, which are arranged on a common optical axis, the light source consisting of multiple diodes which emit light of different wavelengths (LED array), and which are arranged substantially parallel to the optical axis,
b) a controller/analyser, which determines the analyte concentration in the fluid sample on the basis of the measured values supplied by the photodetector,
c) the light source and the photodetector being arranged on or in a sufficiently distortion-resistant and bending-resistant support system, and between them defining a bulbless measurement length, which is automatically filled by immersing the spectrophotometer in the fluid sample to be measured, and the light source and/or the photodetector being movable relative to each other in the beam path, and
d) the portable spectrophotometer being provided with a mains-independent power supply and a digital display for the measurement result.

"Fluid" is the superordinate term for liquids and gases.

The support system for the light source and the photodetector can, for example, be a rail or rod of sufficiently distortion-resistant and bending-resistant plastics material. Suitable plastics materials can be determined by simple tests. The same applies to suitable dimensions of the support system. It is clear that the material properties and dimensions of the support system influence each other. For example, if a material has high bending resistance, a support rail made of it can be thinner. The support system can also be in the form of a tube or pin, for example. The light source and photodetector can then, for example, be arranged on the inside of the tube or pin.

Preferably, the LEDs of the light source emit almost monochromatic light in the wavelength range 200 to 1000 nm, e.g. 250-750 nm or 900 nm. In the case of measurements in gases, the measurement wavelengths can also be in the range 1000 to 5000 nm. In principle, all measurement wavelengths which are useful or desired for a particular measurement problem can be implemented. Multiple different LEDs can be involved, e.g. in the form of an array of LEDs, the emission wavelength ranges of which are different, but can also partly overlap. The wavelength ranges depend on the analytes to be determined. LEDs or LED arrays with suitable wavelength ranges and suitable dimensioning are commercially available. Since the spectral photometer is immersed in the fluid sample for measuring, the light source (e.g. LED or LED array) is in a housing which is sealed against penetration by the fluid, resistant to the fluid, and of suitable dimensions.

As the photodetector, for example a photodiode is used. Photodiodes with suitable sensitivity, spectral bandwidth and suitable dimensions are commercially available. Since the spectral photometer is immersed in the fluid sample for measuring, the photodetector is in a housing which is sealed against penetration by the fluid, resistant to the fluid, and of suitable dimensions.

In the beam path between light sources and photodetector, there are one or more optical elements to steer the light of the emitter efficiently onto the photodetector. These can be implemented as optical lenses, or an arrangement of lenses, or as optical mirrors, or a combination of mirrors and lenses.

To increase the spectral purity of the light which the emitters emit, there can be narrow-band optical filters in the beam path between emitter and photodetector.

Preferably, screens are arranged in the beam path between light source and photodetector, to filter out scattered or reflected light. The screens can be integrated in the fluid-proof housing of the photodetector. In the simplest case, this involves a perforated screen, in which case the incident light from the light source falls through a window which is transparent to light of the chosen wavelength, e.g. a window of quartz glass or of a plastic which is transparent to UV. The light source can also be provided with such a screen, if this is necessary or desired.

The photodetector is connected to an analogue-digital converter, which digitises the received analogue measurement data and thus puts it into a form which can be processed electronically. A programmable microprocessor is responsible for controlling the spectral photometer, e.g. controlling the LEDs, the analogue-digital converter and the digital display, calibration, and analysing the measurement results, e.g. determining the analyte concentration from the measured extinction at a specified measurement wavelength and/or from the measured extinctions at one or more defined measurement wavelengths, the known molar decadic extinction coefficients and the known layer thickness of the fluid sample. The measured values can be converted into a suitable unit and displayed alphanumerically by the digital display. Suitable analogue-digital converters, digital displays and programmable microprocessors or microcontrollers are commercially available, and require no further explanation.

Because of its small dimensions and the mains-independent power supply (e.g. via a battery), the spectral photometer is especially suitable for external use, i.e. outside the laboratory. The ease of use (measurement is by immersion in the fluid sample), in association with the automatic analysis, makes it especially suitable for non-professional users, e.g. for investigating waste water in third world countries or for monitoring swimming pool water.

An advantage of the spectral photometer is that the light source and the photodetector can be moved relative to each other in the beam path in the range 0.5-5 cm, so that layer thicknesses from 0.5 cm to 5 cm can be set. For example, the light source and the photodetector can be movable relative to each other on rails on the support system. Alternatively, the support system itself can be extendable or retractable telescopically, e.g. using a spring mechanism with stops at appropriate distances. In the case of a tubular or pin-shaped support system, a suitable screw thread, which is screwed in or out according to the desired layer thickness, could be used. In principle, there are no special restrictions here, provided that the set distance and thus the layer thickness can be set sufficiently precisely and also remain. The precisely set distance can, for example, be determined using a normally coloured solution, by measuring its extinction and comparing it with its known extinction and concentration using the Lambert-Beer law.

Therefore, differently from the case of known devices, easily variable, e.g. relatively large, layer thicknesses can be set, which may be wanted in the case of very low measurement concentrations. On the other hand, in the case of very high measurement concentrations a smaller layer thickness can easily be set. In the case of the known devices, multiple bulbs with different layer thicknesses would have to be carried to be prepared for all eventualities in external use. Of course, layer thicknesses below 0.5 cm or above 5 cm could also be set, since in principle there is nothing physically against this. What matters here is only the range in which commercially available bulbs are dimensioned.

Of course, too strongly concentrated samples can also be diluted, instead of reducing the layer thickness. Similarly, in the case of too low concentration, the beam path through the fluid sample can also be extended by a mirror system.

The portable spectrophotometer is suitable for measuring a very wide variety of fluids. The fluid sample can be, for example, a gas, a liquid (e.g. also a bodily liquid such as serum) or a mixture of them (e.g. fog or smoke). The type of measured value determination also to some extent makes it possible to measure turbid fluid samples (i.e. thin suspensions of solids in fluids) such as turbid sample waters, interstitial waters, landfill waters, waste water, suspensions of soil samples and fertilisers. Preferably, the portable spectrophotometer is used to determine the concentration of dissolved water content materials. The water sample can be from an aquarium, garden pond or swimming pool, for example. There are no restrictions in relation to the origin of the water.

Examples of water content materials which can be determined using the portable spectrophotometer are oxygen, ozone, chlorine (free chlorine, all chlorine), nitrogen compounds (all nitrogen), potassium, iron, zinc, heavy metals, ammonium, cyanuric acid, cyanide, urea, carbonate (water hardness), hydrogen peroxide, chloride, nitrite, nitrate or phosphate. In particular, using the portable spectrophotometer the pH value of a water sample can also be determined. For this purpose, it is mixed with, for example, a single-component indicator such as phenol red, or with a two-component mixed indicator (e.g. bromothymol blue/thymol blue), which is then measured photometrically. The device automatically recognises the indicator which is used.

Of course, nephelometric turbidity measurements can also be carried out using the portable spectrophotometer.

The portable spectrophotometer can also be used in agriculture and forestry, for checking nutrients in soils.

The portable spectrophotometer is also suitable for measuring gas samples, e.g. for determining the concentration of carbon monoxide, carbon dioxide, water or alcohols or dusts in the air.

Suitable rules (e.g. about acquiring, preparing and handling samples, standards, detection reagents, suitable measurement wavelengths etc.) for photometric determination of many analytes in water are in, for example, "Deutsche Einheitsverfahren (DEV) zur Wasseruntersuchung (German unified procedures for water investigation)", which are familiar to the person skilled in the art.

A further advantage of the portable spectrophotometer is its compatibility with commercially available quick tests or photometric tests. Quick tests for almost any analyte, e.g. for chlorine, can be obtained from the Fluka or Merck companies, for example. In measuring the standards which are supplied with such quick tests for calibration, the portable spectrophotometer automatically detects the measurement method (e.g. the suitable measurement wavelength) to be used, with the aid of a correspondingly programmed database, which for example contains the characteristic absorption spectrum as a spectral "fingerprint". The chosen measurement method is displayed on the digital display of the portable spectrophotometer. However, it is of course also possible to select the measurement method to be used manually. Variations of a particular standard depending on the manufacturer are also taken into account in the database, and corrected if necessary.

An embodiment of the portable spectrophotometer consists substantially of the following components:

A light source in the form of an array of LEDs (e.g. of types OP291A, HLMP-CM36, L-7113UVC, L-53SRC-DV), of which every LED can be controlled individually. To limit the current, series resistors are fitted in each case.

A photodetector in the form of a photodiode (e.g. of type FH229) with an analysis circuit. The photodiode is connected to an operational amplifier (e.g. of type MCP 6001-E/OT), in such a way that the output current Iphoto which the photodiode generates is converted into a voltage Uphoto=Iphoto*10000*V/A which is linearly proportional to the current. The thus obtained voltage is directly proportional to the light intensity falling on the photodiode. The voltage Uphoto is applied to the input of an 18-bit delta sigma analogue-digital converter (e.g. of type MCP 3421A0T-E/OT), and converted by it into a digital signal. The analogue-digital converter also has internal amplification which can be adjusted through software from 1-fold to 8-fold. If necessary, the measurement range can be adjusted in this way.

A microprocessor or microcontroller (e.g. of type PIC18F1220), which is responsible for controlling the LEDs and the analogue-digital converter, controls the course of the measurement and outputs the measured values on a display, in clear text and converted into a suitable unit.

A display, on which the measured values can be output alphanumerically.

A step-up voltage transformer (e.g. of type XC9119D10AMR), which supplies stabilised 5V voltage to the electronics in measurement operation. If the device is in standby, the unstabilised battery voltage of the CR2032 button cell (about 3V, type as example only) is used to supply the processor. To save current, in standby all the peripherals (photodiode, analogue-digital converter and display) are de-energised.

In one embodiment, the mechanical construction resembles a pin, the greater part of the front being taken up by the display. A few buttons make it possible to set the parameters to be measured, and to initiate a measurement.

The measuring cell is part of the housing. Calibration of the portable spectrophotometer can be omitted because of the bulbless operation, since in contrast to known devices, no bulbs which change are used.

The LED array and the photodiode for absorption measurement are on two surfaces of the measuring cell which are plane-parallel to each other, so that the radiation passes directly through the measurement volume, and the transmitted light falls on the photodiode. To screen out ambient light and light from the LEDs which is reflected within the measuring cell, simple screens are provided.

Measurement

An ion concentration C(ion) in the solution to be investigated is assumed.

In a first step, by adding a detection reagent, a colouring complex is formed from the ions. In this case, an excess of the detection reagent is put into the solution, so that complete conversion of all ions to be detected into the colouring complex is given. In the reaction ion+detection reagent→colouring complex+detection reagent the reaction equilibrium is on the right-hand side.

The quantity of formed colouring is thus linearly related to the concentration of the ions:

$$C(colouring)=A*C(ion)$$

The formed colouring shows characteristic absorption bands, which according to what detection reagent is used extend from the infrared range into the ultraviolet range. It is not necessary to measure in the absorption maximum (so-called lambda-max measurement). By the sample being irradiated with the light of a suitably chosen LED, the absorption of the colouring can be measured, and by the Lambert-Beer law the colouring concentration and thus also the ion concentration can be calculated.

Below:

I0 is the intensity of the LED as received by the photodiode, with no colouring complex I is the intensity of the LED as received by the photodiode, with the colouring complex a indicates how sensitively the photodiode reacts to the light of the LED b expresses the specific absorption behaviour of the colouring (a and b are wavelength-dependent)

The Lambert-Beer law $$I/I0=-\exp(-b*C(colouring))$$

indicates the reduction of the transmitted light as a function of the ion concentration.

If the transmittivity $$T=I/I0$$

is known, the ion concentration C(ion) can be deduced from it:

$$C(ion)=C(colouring)/A=-1/(A*b)*\ln(T)$$

The brightness which the photodiode receives consists of two components: the light from the LED, which is radiated through the measuring cell, and the laterally irradiated light from the environment. The photovoltage which the analogue-digital converter converts thus behaves as follows:

$$U\_photo=a*(I(environment)+I(LED))$$

where a is a proportionality factor, which depends on the sensitivity of the LED, the optical construction and the electrical amplification of the photocurrent.

By a dark measurement with the LED switched off $$U\_photo\_dark=a*I(environment)$$

and by subtracting it from the photovoltage with the LED switched on, the apparent brightness of the LED can be determined, apart from the factor a:

$$U\_photo-U\_photo\_dark=a*I(LED)$$

$$=>I(LED)*a=U\_photo-U\_photo\_dark$$

To determine the transmittivity, this measurement must be carried out twice: once with the sample to be investigated, into which no detection reagent has yet been put, and once with the sample mixed with reagent.

The obtained value for I(LED) * a WITHOUT reagent is called I0, and the one WITH reagent is called I.

In calculating the transmittivity T=I/I0, the factor a drops out.

In summary:

$$C(\text{ion}) = -\frac{1}{A \cdot b} \cdot \ln \frac{U_{photo,withcolouring} - U_{photo,dark,withcolouring}}{U_{photo,withoutcolouring} U_{photo,dark,withoutcolouring}}$$

It should be pointed out that the constant a expresses not only the sensitivity of the photodiode to the wavelength which is used, but also a reduction of the light from the LED and the environment, caused by turbidity of the sample. By measuring the apparent brightness of the LED in a first measurement without colouring, this factor can be completely eliminated, so that even slightly turbid samples can be measured.

Determining the Type of Colouring Contained in the Sample

Since LEDs of different colours are built into the spectrometer, it is possible to sample the absorption spectrum of the colouring at several points. The thus obtained point spectrum is characteristic for every colouring, and by comparing it with spectra stored in a database the colouring which is present, and therefore also the ions to be detected, can be deduced. Manual entry of which ions are to be detected is thus omitted.

The invention is explained in more detail below, on the basis of embodiments and with reference to the attached figures of the drawings.

In the figures, the same reference numbers designate the same or functionally equivalent components, unless otherwise indicated.

Figure 1:
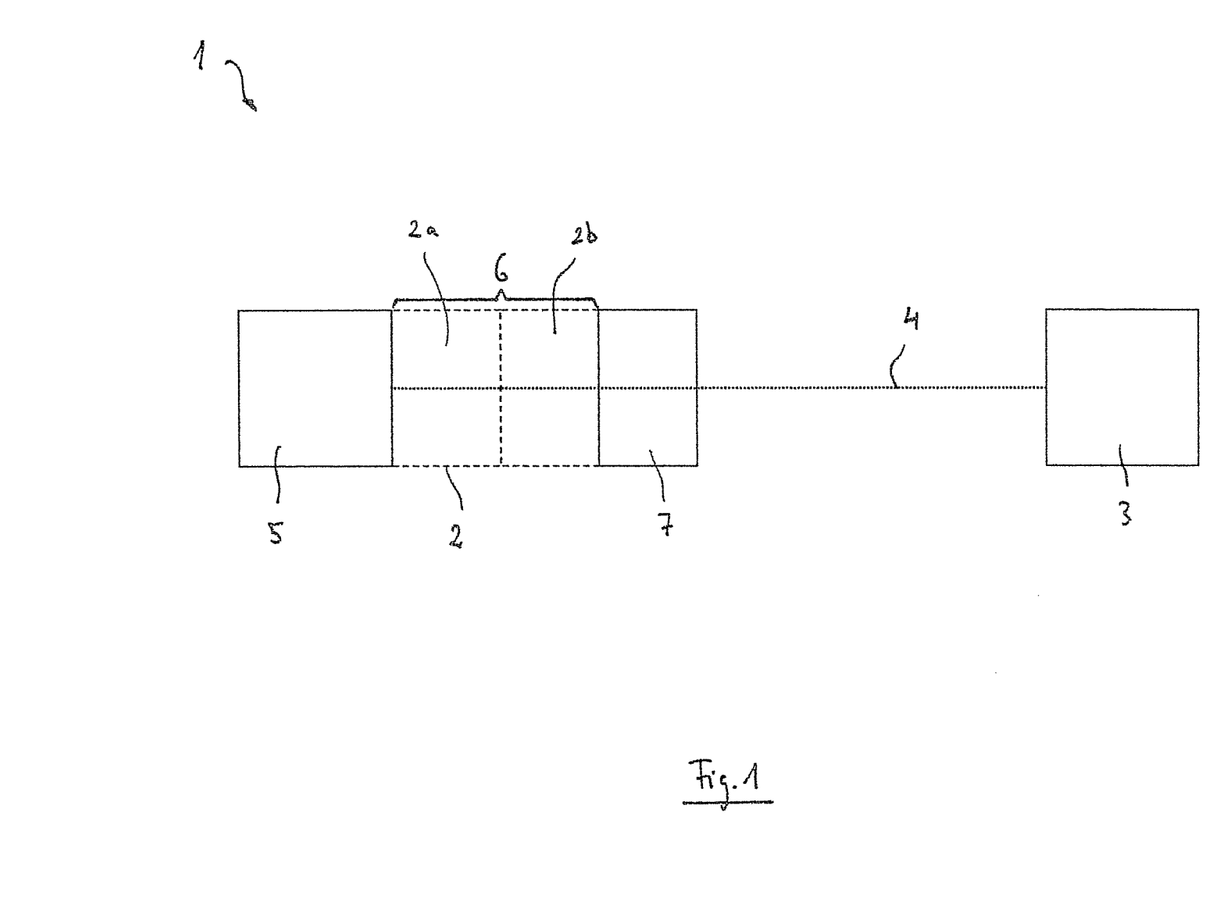
FIG. 1 shows schematically a spectrometer according to an embodiment of the present invention.

FIG. 1 shows schematically a spectrometer 1 according to an embodiment of the present invention.

The spectrometer 1 is a bulbless spectrometer for measuring the concentration of at least one analyte in a fluid sample 2.

The spectrometer 1 has a light source 3 to generate a light beam 4.

The spectrometer 1 also has a photosensor 5 to receive the light beam 4.

The spectrometer 1 also has a measurement length 6 in the beam path of the light beam 4. The fluid sample 2 is placed in the measurement length 6, the volume of the placed fluid sample 2 being determined on the basis of the measurement length 6. In other words, the measurement length 6 specifies a layer thickness of the fluid sample 2, which the light beam 4 must penetrate to reach the photosensor 5 from the light source 3.

The measurement length 6 is provided in changeable form, to change the volume of the fluid sample 2 which can be or is placed in it. In this way, even analytes in very low or very high concentration in the fluid sample 2 can be determined. For example, the measurement length 6, in the case that an analyte which is present only in very low concentration in the fluid sample is involved, is provided relatively large.

By changing the measurement length 6, for example, an initial volume 2a of the fluid sample 2 can be enlarged by an additional volume 2b. The volumes 2a and 2b are shown in FIG. 1 delimited at top and bottom by a dashed line, and at left and right by a continuous line, and a vertical dashed line separates the two volumes 2a and 2b from each other.

The measurement length 6 can now be changed in various ways:

According to the present embodiment, an optical waveguide 7, which is arranged in the beam path of the light beam 4, is provided. The measurement length 6 is defined between the optical waveguide 7 and the photosensor 5. Thus the measurement length 6 can be changed by moving either the photosensor 5 relative to the optical waveguide 7 or the optical waveguide 7 relative to the photosensor 5.

Alternatively, it is also conceivable that the measurement length 6 is defined directly between the photosensor 5 and the light source 3, i.e. the optical waveguide 7 is dispensed with. The measurement length 6 is then changed by moving either the photosensor 5 relative to the light source 3 or the light source 3 relative to the photosensor 5.

The movements described above refer to a movement along the beam path of the light beam 4.

Also, the photosensor 5 and the light source 3 in the embodiment according to FIG. 1 could also be exchanged, meaning that the measurement length 6 is defined between the light source 3 and the optical waveguide 7.

The described spectrometer 1 thus does completely without the bulbs described in the introduction, i.e. in particular no bulb is required for measuring the concentration of the analyte. It is therefore a bulbless spectrometer 1.

Figure 2:
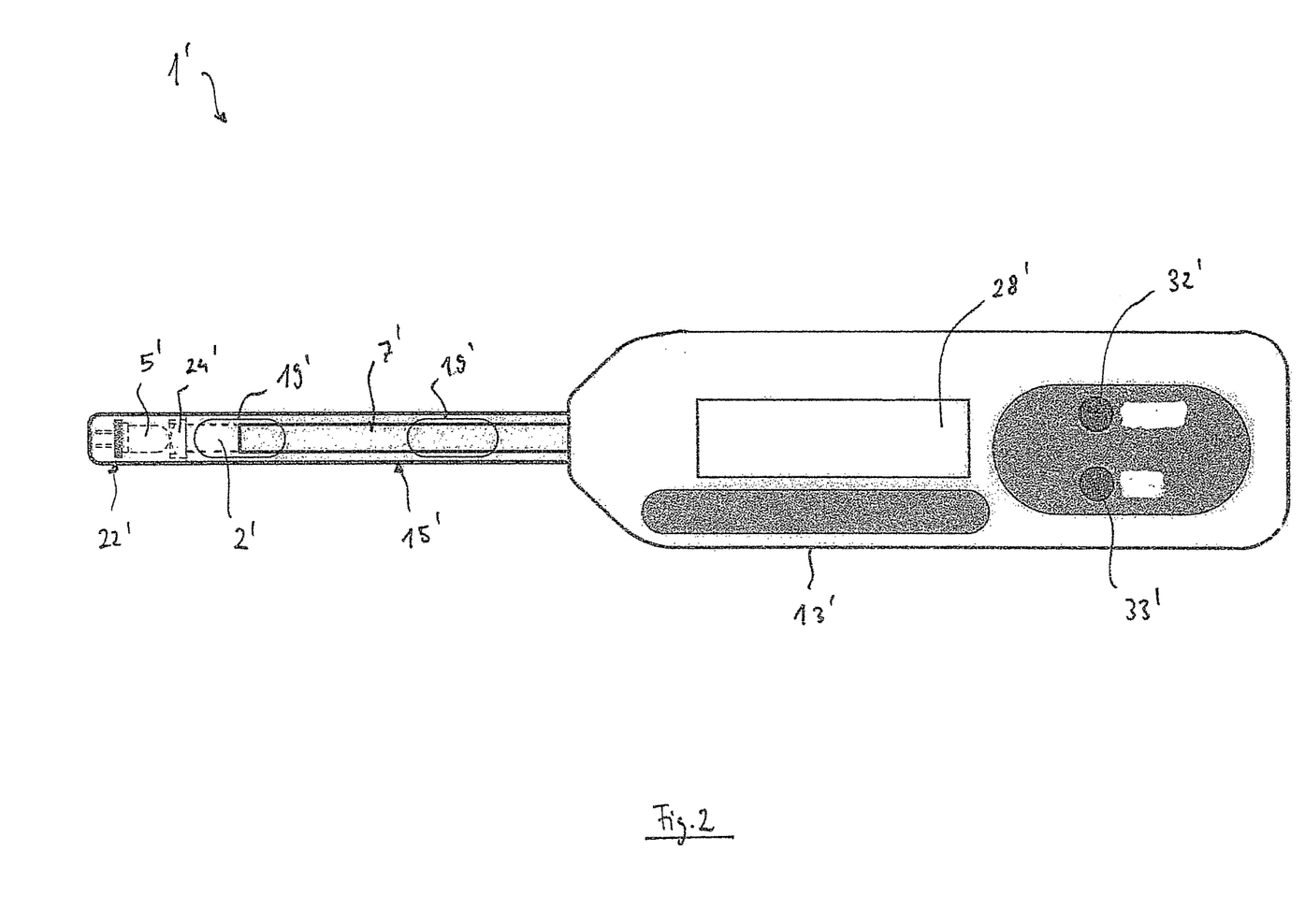
FIG. 2 shows, in a plan view, a spectrometer according to another embodiment of the present invention, the sleeve being shown partly transparently.

Below, a spectrometer 1' for which the explanations about FIG. 1 apply correspondingly is described in relation to FIGS. 2-4.

The bulbless spectrometer 1' is used to measure the concentration of at least one analyte in a fluid sample 2'. In FIG. 2, the fluid sample 2' is shown delimited at top and bottom by a dashed line, and at each side by two continuous lines.

The fluid sample 2' can be a gas, a liquid or a mixture of them. The fluid sample 2 can also include a certain solid part, e.g. dust.

The analyte is preferably a content material which is preferably dissolved in water. Examples of such content materials are oxygen, ozone, chlorine (free chlorine, all chlorine), nitrogen compounds (all nitrogen), magnesium, calcium, copper, potassium, iron, zinc, heavy metals, ammonium, cyanuric acid, cyanide, urea, carbonate (water hardness), hydrogen peroxide, chloride, nitrite, nitrate or phosphate. However, the fluid sample 2' can equally well be a gas, in particular air. By means of the spectrometer 1', for example the concentration of carbon monoxide, carbon dioxide, water contents, alcohols, turbidities, dusts in the air can be measured. For example, the fluid samples 2' can also be soil samples or fertilisers. It is also possible to measure a pH value in the fluid sample 2' using the spectrometer 1'.

Depending on the fluid sample 2' and/or the analyte, it may be necessary first to put a surplus of an indicator into the fluid sample 2' or into the fluid 20'. For example, to determine a pH value, the fluid sample 2' or the fluid 20' can be mixed with phenol red.

Figure 3:
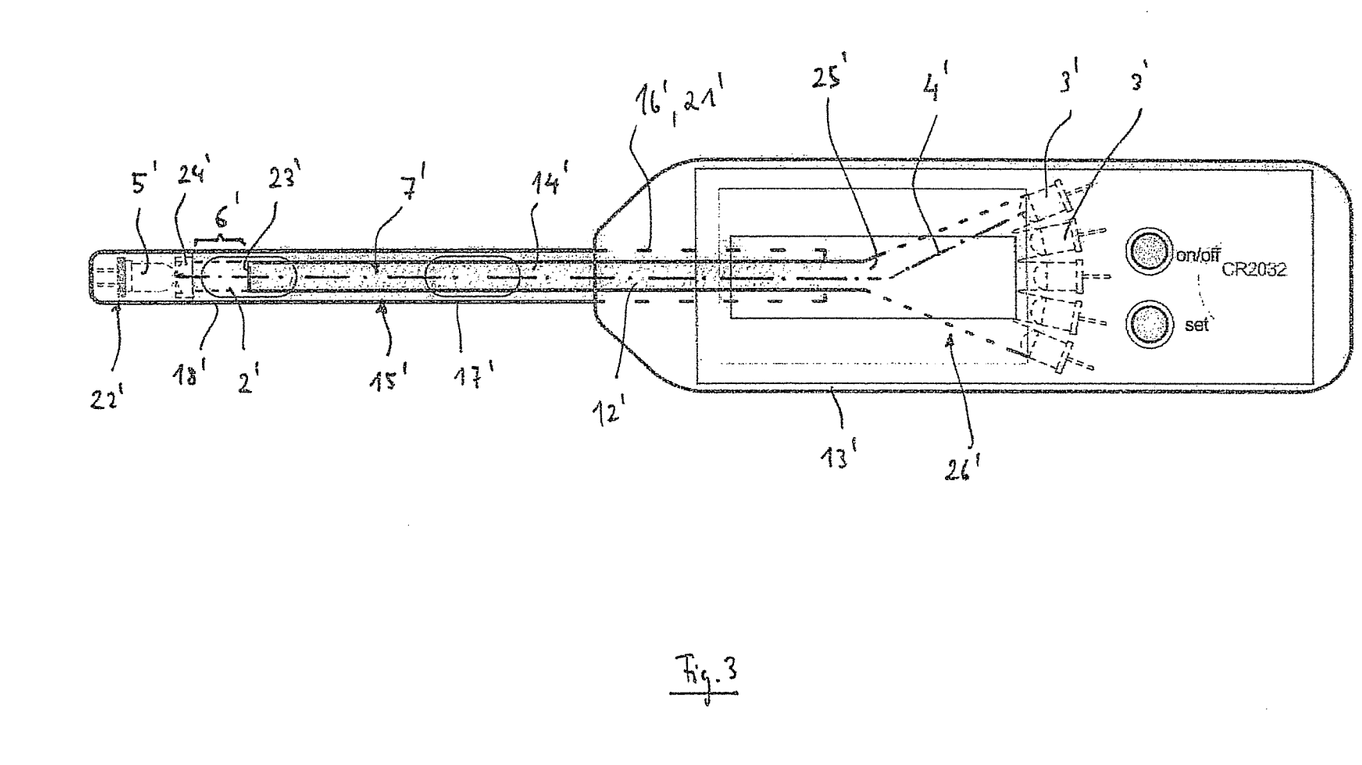
FIG. 3 shows the view from FIG. 2, the handling part also being shown partly transparently.

The spectrometer 1' has multiple light sources 3', see FIG. 3. The light sources 3' are preferably LEDs, more preferably laser LEDs. The light sources 3' are set up to emit almost monochromatic light with a wavelength of preferably 250-750 nm. Preferably, the light sources 3' are each set up to emit light of different wavelengths or different wavelength ranges. For example, one light source 3' can be set up to emit light with a wavelength between 610 and 750 nm, and the other light source 3' can be set up to emit light with a wavelength between 590 and 610 nm. The choice of the light source 3' can depend on the fluid sample 2' and/or the analyte concentration which is to be measured, and also be selected automatically, as will be described in more detail below.

The one or more light sources 3' generate a light beam 4', which is indicated in FIG. 3 by a dashed-dotted line. The multiple light sources 3 can be arranged approximately in a semicircle, and more preferably form an array.

The spectrometer 1' also has a photosensor 5' to receive the light beam 4'. The photosensor 5' converts the incident light beam 4' into electrical signals. The electrical signals depend on the incident luminous power and/or wavelength of the light beam 4'. The photosensor 5 is preferably a photodiode.

The spectrometer 1 is also in a form with a measurement length 6' in the beam path of the light beam 4'. The fluid sample 2' can be placed in the measurement length 6', the volume of the fluid sample 2' which can be placed being determined on the basis of the measurement length 6', as explained above in relation to FIG. 1.

The measurement length 6' is provided so that it can be changed, in order to change the volume of the fluid sample 2' which can be placed in it. For this purpose, for example the spectrometer 1 is in the following form:

In the beam path of the light beam 4', an optical waveguide 7' in the form of an acrylic bar, MacroIon bar, glass bar or glass fibre cable is arranged.

The optical waveguide 7 has a first section 12', which is housed permanently in a handling part 13' in the form of a housing. The optical waveguide 7' also has a second section 14', which extends out of the handling part 13' into a sleeve 15'.

The sleeve 15' has an substantially annular cross-section. The internal diameter of the annular cross-section of the sleeve 15' corresponds substantially to the external diameter of the circular cross-section of the optical waveguide 7'.

The sleeve 15' is preferably provided with multiple long holes 19'. Two long holes 19' can be opposite each other, as shown in FIG. 4. Also, for example, two such pairs of long holes 19' opposite each other along the beam path of the light beam 4' can be provided at a distance from each other along the sleeve 15'. Irrespective of the position of the sleeve 15' relative to the handling part 13' and/or the optical waveguide 7', one of the long holes 19' is always connected to the measurement length 6', meaning that the fluid sample 2' can be taken from the fluid 20', e.g. a body of water. According to the present embodiment, such samples can be taken simply by immersing the long holes 19', and thus also immersing the sleeve 15' with the end piece 22', in the fluid 20'.

The sleeve 15' has a first section 16', with which it extends into the handling part 13'. The section 16' is received so that it can move along the beam path of the light beam 4' in a receiving space 21' of the handling part 13'. For example, the section 16' can be provided with an external thread, which engages with a corresponding internal thread in the handling part 13'. Alternatively, the section 16' can be provided on the outside with catches, which engage with corresponding counter-catches in the handling part 13', and thus make step-by-step mobility of the sleeve 15' relative to the handling part 13' possible.

A second section 17' of the sleeve 15' extends outward from the handling part 13', and thus surrounds the second section 14' of the optical waveguide 7'. A third section 18' of the sleeve 15' is connected to the second section 17' of the sleeve 15', and delimits the fluid sample 2' at its perimeter. An end piece 22' is in turn connected to the third section 18'. The and piece 22' forms a fluid-proof seal for the annular cross-section of the sleeve 15'.

The measurement length 6' is thus defined between the end piece 22' and a face 23' of the optical waveguide 7'. The volume of the fluid sample 2' is delimited along the beam path of the light beam 4' by the end piece 22' and the face 23', and, as mentioned, delimited at its perimeter by the third section 18' of the sleeve 15'.

The end piece 22' has the photosensor 5' and preferably a lens 24', which focuses the incident light beam 4' onto the photosensor 5'.

By moving the sleeve 15' in or out of the receiving region 21' of the handling part 13', the measurement length 6' is set, and can thus easily be adjusted for the requirements for measuring the concentration of an analyte. It is also conceivable here that the sleeve is moved in and out of the handling part 13' in an automated manner, e.g. by means of an appropriate servomotor.

On the other face 25' of the optical waveguide 7', the light beam 4' is coupled in. Means 26' can be provided to connect one or the other light source 3', according to choice, to the optical waveguide 7', to carry light.

Figure 4:
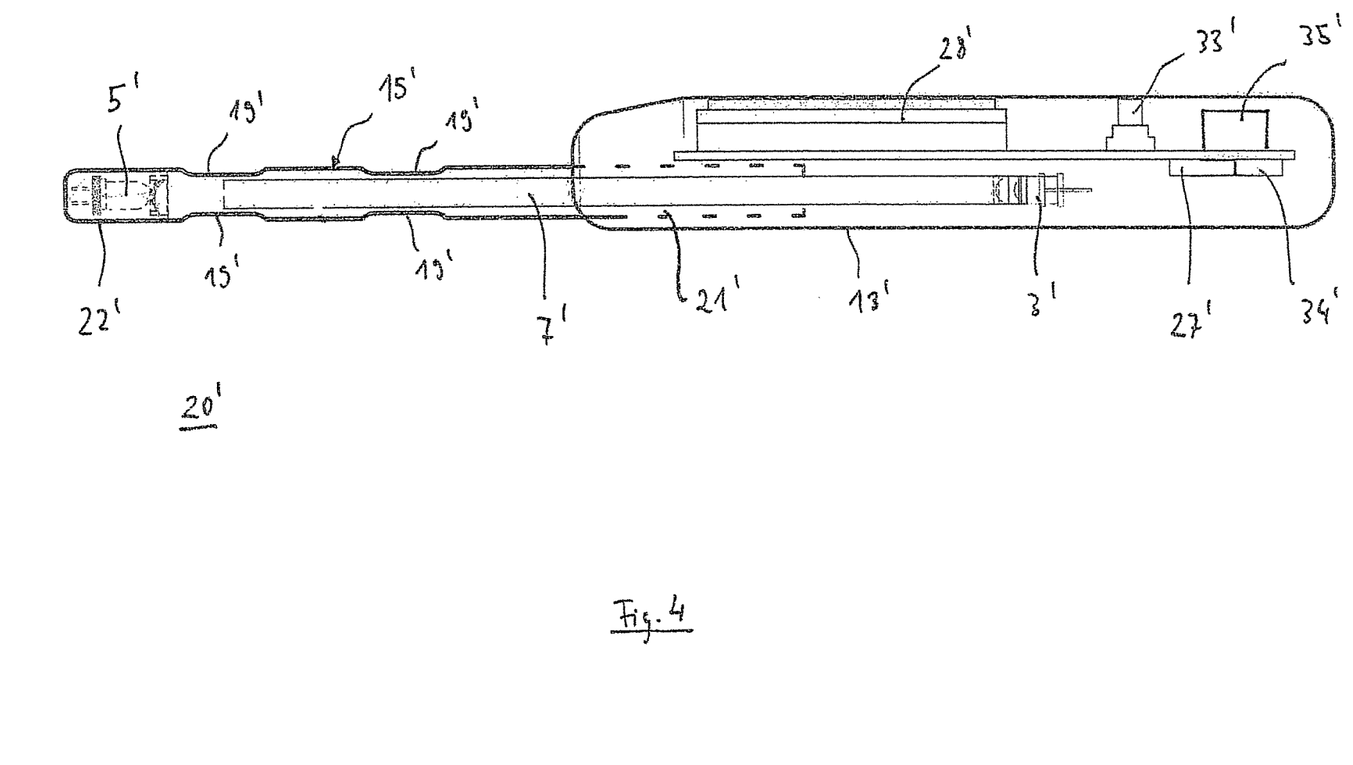
FIG. 4 shows a side view from FIG. 3.

The spectrometer 1' also has a controller 27', see FIG. 4, which controls the light sources 3'. The controller 27' also controls the photosensor 5', e.g. to calibrate it. The photosensor 5' also feeds the electrical signals which it generates to the controller 27', for analysis by it.

The spectrometer 1 is also designed with a display 28' for displaying, for example, the measured analyte concentrations. A menu selection, by means of which a user can operate the controller 27', can also be shown on the display 28'.

The spectrometer 1' can have, in addition to an on/off button 32', further controls 33', by means of which controlling the menu of the display 28' and corresponding selection are made possible.

The spectrometer 1' can also have a memory 34', which for example is integrated into the controller 27'. In the memory 34', various analysis modes can be stored. For example, a user who wants to determine the concentration of a specified analyte, e.g. oxygen, can select, using the menu selection of the display 28', a corresponding analysis mode which is stored in the memory 34'. The controller 27', depending on the selected analysis mode, then controls the light sources 3' and the photosensor 5' appropriately, and carries out appropriate analyses, which are then shown on the display 28'.

Additionally or alternatively, an analysis as described below can take place, a suitable analysis mode being selected in an automated manner: In a first step, the controller 27' controls the multiple light sources 3' and the photosensor 5', to determine a characteristic of the fluid sample 2'. The characteristic is, for example, a specific absorption spectrum of the fluid sample 2'. In a second step, the controller 27' selects one of multiple analysis modes which are stored in the memory 34', depending on the characteristic. For example, the determined characteristic can be compared with characteristics stored in the memory 34', and if there is appropriate agreement, the analysis mode associated with a stored characteristic is selected. Then, in a third step, the light sources 3' and the photosensor 5' are controlled depending on the selected analysis mode, and appropriate analyses of the signals from the photosensor 5' are carried out.

By using the above method steps, therefore, the spectrometer 1 can determine automatically what type of fluid sample 2' is involved, e.g. a fertiliser, and then select the suitable analysis mode for it, whereupon the concentrations of the relevant analytes for the fluid sample are measured and shown on the display 28'. In particular, selecting from among the multiple light sources 3' a particular light source 3', which is used to determine the concentration of a specified analyte in the fluid sample 2', can be done depending on the analysis mode.

Preferably, in particular the controller 27', the display 28', the controls 32', 33' and the memory 34' are integrated in the handling part 13' and housed so that they are protected from environmental influences, in particular liquid and dust.

The handling part 13' also has an energy source 35', e.g. in the form of a rechargeable battery, which supplies energy to the electrical components 3', 5', 27', 28', 33' and 34'.

Additionally, the spectrometer 1' can have a data interface, e.g. a USB connection or an RS-232 connection, to control the spectrometer 1' and/or its electrical components 3', 5', 27', 28', 33' and 34' externally and/or to supply energy to them.

The result is a construction for the spectrometer 1' which makes it possible to transport and handle it easily manually. The spectrometer 1' is thus also independent of the mains. Of course, it is equally conceivable to supply energy to the spectrometer 1' from a mains power supply. The spectrometer 1' can also be provided in stationary form, e.g. for measuring turbidity in pipes. The spectrometer 1' can also be used as a signal transmitter for automatic titration states in a laboratory.

In a version of the spectrometer 1', it can be designed with the following electronic components:

- multiple light sources 3' in the form of an array of LEDs (e.g. of types TSAL5300. MARL: 100041, HLMP-Y801, TLSH180P), of which every LED can be controlled individually; to limit the current, series resistors are fitted in each case;
- a photosensor 5' in the form of a photodiode (e.g. of type OP950) with an analysis circuit; the photodiode is connected to an operational amplifier (e.g. of type OP07), in such a way that the output current Iphoto which the photodiode generates is converted into a voltage Uphoto ∝ Iphoto which is linearly proportional to the current; the thus obtained voltage is directly proportional to the light intensity falling on the photodiode; the voltage Uphoto is applied to the input of an analogue-digital converter (e.g. of type AD7450), and converted by it into a digital signal;
- a controller 27' in the form of a microprocessor or microcontroller (e.g. of type MC9S08QG8CDTE), which is responsible for controlling the LEDs 3' and the analogue-digital converter, controls the course of the measurement and outputs the measured values on the display 28' in the form of a screen, in clear text and converted into a suitable unit;
- a display, on which the measured values can be output alphanumerically; and/or
- a step-up voltage transformer (e.g. of type NCP1400A), which supplies stabilised 5V voltage to the electronics in measurement operation; if the spectrometer 1 is in standby, the unstabilised battery voltage of the CR2032 button cell (about 3V, type as example only) is used to supply the processor; to save current, in standby all the peripherals (photodiode, analogue-digital converter and display) are de-energised.

The spectrometer 1, 1' can be used to determine the volume of a fluid in a vessel. Specifically, the determination of the volume of a pond could take the following form:

First, a volume of one litre of water is measured. A teaspoon of a compound containing calcium ions is put into the water. Next, using the spectrometer 1, 1', the concentration of the calcium ions in the one litre of water is determined; it is called the first concentration below.

The litre of water is then put into a pond, and there is a wait for a certain time until the calcium ions have distributed themselves in the pond.

Next, using the spectrometer 1, 1', the concentration of the calcium ions in the pond is determined; it is called the second concentration below.

Next, a defined analysis mode of the spectrometer 1, 1' is started; on the basis of the first and second concentrations and of the volume of one litre of water, it determines the volume of the pond.

Thus, in particular, pond owners can easily determine the volume of their pond.

Although the invention has been described here on the basis of preferred embodiments, it is not restricted to them, but can be modified in many ways.

Below, further embodiments of the invention are presented:

1. Portable bulbless immersion spectrophotometer for determining analyte concentrations in fluid samples, with
a) a light source and a photodetector, which are arranged on a common optical axis, the light source consisting of multiple diodes which emit light of different wavelengths (LED array) or laser diodes, and which are arranged substantially parallel to the optical axis,
b) a controller/analyser, which determines the analyte concentration in the fluid sample on the basis of the measured values supplied by the photodetector,
c) the light source and the photodetector being arranged on or in a sufficiently distortion-resistant and bending-resistant support system, and between them defining a bulbless measurement length, which is automatically filled by immersing the spectrophotometer in the fluid sample to be measured, and the light source and/or the photodetector being movable relative to each other in the beam path, and
d) the portable spectrophotometer being provided with a mains-independent power supply and a digital display for the measurement result.

2. Portable spectrophotometer according to embodiment 1, characterised in that the LEDs emit almost monochromatic light of wavelengths 250-750 nm.

3. Portable spectrophotometer according to either embodiment 1 or embodiment 2, characterised in that the photodetector is a photodiode.

4. Portable spectrophotometer according to any one of the preceding embodiments, characterised in that screens are arranged in the beam path between light source and photodetector, to filter out scattered or reflected light.

5. Portable spectrophotometer according to any one of the preceding embodiments, characterised in that the photodetector is connected to an analogue-digital converter.

6. Portable spectrophotometer according to any one of the preceding embodiments, characterised in that the controller/analyser is based on a programmable microprocessor.

7. Portable spectrophotometer according to embodiment 6, characterised in that the microprocessor is responsible for controlling the LEDs, the analogue-digital converter and the digital display.

8. Portable spectrophotometer according to any one of the preceding embodiments, characterised in that the digital display displays the measured values alphanumerically and converted into a suitable unit.

9. Portable spectrophotometer according to any one of the preceding embodiments, characterised in that the light source and the photodetector can be moved relative to each other in the beam path in the range 0.5-5 cm.

10. Portable spectrophotometer according to any one of the preceding embodiments, characterised in that the mains-independent power supply is a battery.

11. Portable spectrophotometer according to any one of the preceding embodiments, characterised in that the fluid sample to be measured is a gas, a liquid or a mixture of them.

12. Use of the portable spectrophotometer according to any one of the preceding embodiments, to determine the concentration of dissolved water content materials.

13. Use according to embodiment 12, the dissolved water content materials being selected from oxygen, ozone, chlorine (free chlorine, all chlorine), nitrogen compounds (all nitrogen), magnesium, calcium, copper, potassium, iron, zinc, heavy metals, ammonium, cyanuric acid, cyanide, urea, carbonate (water hardness), hydrogen peroxide, chloride, nitrite, nitrate or phosphate.

14. Use of the portable spectrophotometer according to any one of the preceding embodiments, for checking nutrients in soils in agriculture and forestry.

15. Use of the portable spectrophotometer according to any one of the preceding embodiments, to determine the concentration of carbon monoxide, carbon dioxide, water contents, alcohols, turbidities and dusts in the air, of content materials in suspensions of soil samples and fertilisers.

16. Use of the portable spectrophotometer according to any one of the preceding embodiments, to determine the concentration of dissolved water content materials also in a stationary technical variant embodiment.

The further developments and embodiments described here for the portable spectrophotometer apply correspondingly to the described bulbless spectrometer, and vice versa.

REFERENCE NUMERALS 1, 1' spectrometer
2, 2' fluid sample
2a volume
2b volume
3 light source
3, 3' light source
4, 4' light beam
5, 5' photosensor
6, 6' measurement length
7, 7' optical waveguide
12' first section
13' handling part
14' second section
15' sleeve
16' first section
17' second section
18' third section
19' long hole
20' fluid
21' receiving region
22' end piece
23' face
24' lens
25' face
26' means
27' controller
28' display
32' on/off button
33' control
34' memory
35' energy source

The invention claimed is:

1. A bulbless spectrometer for measuring the concentration of at least one analyte in a fluid sample,
with a light source to generate a light beam,
with a photosensor to receive the light beam, and
with a measurement length, in which the fluid sample can be placed, in the beam path of the light beam,
the measurement length being provided in changeable form, wherein
the light source and the photodetector are provided so that they can move relative to each other in order to change the measurement length, and
the measurement length is formed between the light source or the photosensor and an optical waveguide arranged in the beam path,
and the light source and the optical waveguide and/or the photosensor and the optical waveguide are provided so that they can move relative to each other in order to change the measurement length, wherein
the optical waveguide extends into a sleeve, the measurement length is formed between one face of the optical waveguide and an end piece, which seals the sleeve, and the measurement length is changeable by moving the sleeve and the optical waveguide relative to each other.

2. The spectrometer according to claim 1, wherein
the sleeve has at least one opening, which makes it possible to place the fluid sample in the measurement length.

3. The spectrometer according to claim 2, wherein
along the beam path two of the openings are provided in the sleeve at a distance from each other.

4. The spectrometer according to any one of claims 1 to 3, wherein
the optical waveguide is attached permanently to a handling part of the spectrometer, and/or the sleeve extends in sections in a receiving region in the handling part, and the sleeve is provided so that it can move within the receiving region.

5. The spectrometer according to claim 4, wherein the end piece of the sleeve, which seals the sleeve, has a lens and/or the photosensor.

6. The spectrometer according to claim 4, wherein
the light source couples in the light beam on the other face of the optical waveguide.

7. The spectrometer according to claim 4, wherein
the optical waveguide is in the form of an acrylic bar, Macrolon bar, glass bar or glass fibre cable.

8. The spectrometer according to any one of claims 1 to 5, wherein
the end piece of the sleeve, which seals the sleeve, has a lens and/or the photosensor.

9. The spectrometer according to any one of claims 1 to 5, wherein
the light source couples in the light beam on the other face of the optical waveguide.

10. The spectrometer according to any one of claims 1 to 5, wherein
the optical waveguide is in the form of an acrylic bar, Macrolon bar, glass bar or glass fibre cable.

11. The spectrometer according to claim 1, wherein
a first light source and at least one second light source are provided, so that the light beam can be generated with a first or at least a second wavelength or a wavelength range according to choice.

12. The spectrometer according to claim 1, wherein
the one or more light sources are in the form of LEDs.

13. The spectrometer according to claim 12, wherein the one or more light sources are in the form of laser diodes.

14. The spectrometer according to claim 1, wherein
a controller is provided, and said controller, controls the one or more light sources and the photosensor so as to determine a characteristic of the fluid sample; selects one of multiple analysis modes, which are stored in a memory of the spectrometer, depending on the characteristic; and controls the one or more light sources and the photosensor depending on the selected analysis mode.

15. The spectrometer according to claim 1, wherein the spectrometer is in portable and/or mains-independent form.

16. The spectrometer according to claim 1, wherein the optical waveguide is attached permanently to a handling part of the spectrometer.

17. A method for determining a volume of a fluid in a vessel, the method comprising using a spectrometer, the spectrometer being a bulbless spectrometer for measuring the concentration of at least one analyte in a fluid sample, with a light source to generate a light beam, with a photosensor to receive the light beam, and with a measurement length, in which the fluid sample can be placed, in the beam path of the light beam, the measurement length being provided in changeable form; wherein (a) the light source and the photodetector are provided so that they can move relative to each other in order to change the measurement length; and (b) the measurement length is formed between the light source or the photosensor and an optical waveguide arranged in the beam path, and the light source and the optical waveguide and/or the photosensor and the optical waveguide are provided so that they can move relative to each other in order to change the measurement length; and (c) the optical waveguide extends into a sleeve, the measurement length is formed between one face of the optical waveguide and an end piece, which seals the sleeve, and the measurement length is changeable by moving the sleeve and the optical waveguide relative to each other.

* * * * *

UNITED STATES PATENT AND TRADEMARK OFFICE
CERTIFICATE OF CORRECTION

PATENT NO. : 8,582,103 B2  
APPLICATION NO. : 13/375396  
DATED : November 12, 2013  
INVENTOR(S) : Willuweit et al.

Page 1 of 1

It is certified that error appears in the above-identified patent and that said Letters Patent is hereby corrected as shown below:

On the Title Page

On column 1, line 7, item (73)
  replace "und"
  with --Und--.

On column 1, line 8, item (73)
  replace "Etwicklungs"
  with --Entwicklungs--.

Signed and Sealed this
Eleventh Day of February, 2014

Michelle K. Lee
*Deputy Director of the United States Patent and Trademark Office*